US00PP19507P2

(12) United States Plant Patent
van den Top

(10) Patent No.: US PP19,507 P2
(45) Date of Patent: Nov. 25, 2008

(54) *HOSTA* PLANT NAMED 'SECRET AMBITION'

(50) Latin Name: ***Hosta* hybrid**
Varietal Denomination: Secret Ambition

(76) Inventor: Hendrik Jan van den Top, Wesselseweg 46, 3771 PC Barneveld (NL)

( * ) Notice: Subject to any disclaimer, the term of this patent is extended or adjusted under 35 U.S.C. 154(b) by 0 days.

(21) Appl. No.: 12/012,480

(22) Filed: Jan. 31, 2008

(51) Int. Cl.
*A01H 5/00* (2006.01)

(52) U.S. Cl. ..... Plt./353

(58) Field of Classification Search ..... Plt./353
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Hosta* plant named 'Secret Ambition', characterized by its broadly spreading foliage with upright flower scapes; green and light green variegated foliage; light violet to white-colored flowers that are positioned above the foliage on strong scapes; and good garden performance.

2 Drawing Sheets

Botanical designation: *Hosta* hybrid.
Cultivar denomination: 'Secret Ambition'.

BACKGROUND OF THE INVENTION

The present invention relates to a new and distinct cultivar of *Hosta,* botanically known as *Hosta* hybrid and hereinafter referred to by the name 'Secret Ambition'.

The new *Hosta* is a naturally-occurring whole plant mutation of the *Hosta* hybrid cultivar Secret Love, not patented. The new *Hosta* was discovered and selected by the Inventor in a controlled greenhouse environment in Barneveld, The Netherlands during the spring of 2004.

Asexual reproduction of the new *Hosta* by divisions in a controlled environment in Barneveld, The Netherlands since July, 2006, has shown that the unique features of this new *Hosta* are stable and reproduced true to type in successive generations.

SUMMARY OF THE INVENTION

The cultivar Secret Ambition has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Secret Ambition'. These characteristics in combination distinguish 'Secret Ambition' as a new and distinct cultivar of *Hosta:*

1. Broadly spreading foliage with upright flower scapes.
2. Green and light green variegated foliage.
3. Light violet to white-colored flowers that are positioned above the foliage on strong scapes.
4. Good garden performance.

Plants of the new *Hosta* differ from plants of the parent, the cultivar Secret Love, primarily in leaf coloration as leaves of plants of the new *Hosta* have a broader light green-colored edge than leaves of plants of the cultivar Secret Love.

Plants of the new *Hosta* can be compared to plants of the cultivar Sweet Innocence, not patented. In side-by-side comparisons conducted in Barneveld, The Netherlands, plants of the new *Hosta* and the cultivar Sweet Innocence differed primarily in leaf coloration as plants of the cultivar Sweet Innocence had light green and pale yellow variegated foliage.

BRIEF DESCRIPTION OF THE PHOTOGRAPHS

The accompanying colored photographs illustrate the overall appearance of the new *Hosta,* showing the colors as true as it is reasonably possible to obtain in colored reproductions of this type. Colors in the photographs may differ slightly from the color values cited in the detailed botanical description which accurately describe the colors of the new *Hosta.*

The photograph on the first sheet comprises a side perpsective view of a typical flowering plant of 'Secret Ambition' grown in a container.

The photograph at the top of the second sheet is a close-up view of the upper surfaces of typical developing (left) and fully expanded (right) leaves of 'Secret Ambition'.

The photograph at the bottom of the second sheet is a close-up view of the lower surfaces of typical developing (left) and fully expanded (right) leaves of 'Secret Ambition'.

DETAILED BOTANICAL DESCRIPTION

The aforementioned photographs and following observations, measurements and values describe plants grown in containers in Barneveld, The Netherlands, under commercial practice during the late summer in an outdoor nursery with day temperatures ranging from 14° C. to 35° C. and night temperatures ranging from 5° C. to 18° C. Plants had been growing for about 14 months when the photographs and description were taken. In the following description, color references are made to The Royal Horticultural Society Colour Chart, 2001 Edition, except where general terms of ordinary dictionary significance are used.

Botanical classification: *Hosta* hybrid cultivar Secret Ambition.

Parentage: Naturally-occurring whole plant mutation of the *Hosta* hybrid cultivar Secret Love, not patented.

Propagation:

*Type.*—By divisions.

*Root description.*—Medium thickness, fibrous; creamy white in color.

*Rooting habit.*—Moderate branching.

Plant description:

*Plant form/habit.*—Herbaceous flowering perennial plant. Mounded plant form with broadly spreading foliage with upright flower scapes. Flowering stems and leaves basal; moderately vigorous growth habit. Light violet to white-colored flowers are positioned above the foliage on strong scapes.

*Growth rate.*—Moderately fast; about one year are required to produce fully-grown flowering plants.

*Plant height* (*soil level to top of foliar plane*).—About 15 cm.

*Plant height* (*soil level to top of inflorescences*).—About 40 cm.

*Plant width* (*spread*).—About 30 cm.

Foliage description:

*Arrangement/form.*—Leaves basal, simple, generally symmetrical and long-persisting.

*Leaf length.*—About 9 cm to 12 cm.

*Leaf width.*—About 4.5 cm to 8.5 cm.

*Shape.*—Cordate.

*Apex.*—Cuspidate.

*Base.*—Truncate to rounded.

*Margin.*—Entire.

*Texture, upper and lower surfaces.*—Smooth, glabrous; leathery; moderately rugose.

*Venation pattern.*—Pinnate, arcuate.

*Color.*—Developing leaves, upper surface: Center, close to 191A; towards the margins, close to 144A to 144B. Developing leaves, lower surface: Center, close to 191B; towards the margins, close to 144B. Fully expanded leaves, upper surface: Center, close to 137A, 137B and/or 137C; towards the margins, close to 160C to 160D; venation, similar to lamina. Fully expanded leaves, lower surface: Center, close to 191A; towards the margins, more green than 160D; venation, similar to lamina.

*Petiole length.*—About 6 cm to 10 cm.

*Petiole diameter.*—About 6 mm to 8 mm.

*Petiole texture, upper and lower surfaces.*—Smooth, glabrous.

*Petiole color, upper surface.*—Close to 137C; towards the margins, 144C.

*Petiole color, lower surface.*—Close to 144A to 144B; towards the margins, 144C.

Flower description:

*Flower type/habit.*—Numerous single campanulate flowers with fused perianth arranged on terminal racemes; flowers face outward or slightly downward. Panicles roughly conical in shape. Freely flowering habit with about 15 flowers developing per inflorescence.

*Fragrance.*—Faintly to moderately fragrant; sweet, pleasant.

*Natural flowering season.*—Recurrent flowering throughout the summer in The Netherlands.

*Postproduction longevity.*—Flowers last about one week on the plant. Flowers not persistent.

*Flower buds.*—Height: About 1 cm to 3 cm. Diameter: About 6 mm to 11 mm. Shape: Ovate. Color: Close to 145B to 145D.

*Inflorescence height.*—About 12 cm to 14 cm.

*Inflorescence diameter.*—About 12 cm to 14 cm.

*Flower diameter.*—About 4 cm.

*Flower depth.*—About 5 cm.

*Perianth.*—Arrangement: Three interior tepals arranged in a single whorl surrounded by an outer whorl of three exterior tepals. Tepal length: About 2 cm to 2.5 cm. Tepal width: About 1 cm to 1.8 cm. Tepal shape: Ovate. Tepal apex: Acute. Tepal margin: Entire. Tepal texture, upper and lower surfaces: Smooth, glabrous; satiny. Tepal color: Developing and fully expanded petals, upper surface: Close to between 85D and N155A. Developing and fully expanded petals, lower surface: Close to 85D.

*Flower bracts.*—Quantity: One per flower at the base of the pedicel. Length: About 1.5 cm. Width: About 5 mm. Shape: Ovate. Apex: Acute. Base: Cuneate. Margin: Entire. Texture, upper and lower surfaces: Smooth, glabrous. Color, upper and lower surfaces: Towards the base, close to 145D; towards the apex, 145B.

*Peduncles* (*scapes*).—Length: About 35 cm to 40 cm. Diameter: About 4 mm to 5 mm. Angle: Erect. Strength: Strong. Texture: Smooth, glabrous. Color: Close to 146B.

*Pedicels.*—Length: About 1.2 cm to 1.4 cm. Diameter: About 2 mm. Strength: Moderately strong. Texture: Smooth, glabrous. Color: Close to 146B.

*Reproductive organs.*—Stamens: Quantity per flower: Typically six; anthers dorsifixed. Filament length: About 5.5 cm. Filament color: Close to 155D. Anther shape: Narrowly oblong. Anther length: About 5 mm. Anther color: Close to 199B to 199C. Pollen amount: Moderate. Pollen color: Close to 160A.

*Pistils.*—Quantity per flower: One. Stigma shape: Lobed. Stigma color: Close to 155D. Style length: About 5.5 cm. Style color: Close to 155D. Ovary length: About 8 mm to 10 mm. Ovary color: Close to 145B.

*Seed/fruit.*—Seed and fruit development have not been observed.

Disease/pest resistance: Plants of the new *Hosta* have not been noted to be resistant to pathogens and pests common to *Hosta*.

Garden performance: Plants of the new *Hosta* have been observed to have good garden performance and tolerate rain, wind and high temperatures of about 35° C. Plants of the new *Hosta* have been observed to be hardy to USDA Zone 5.

It is claimed:

1. A new and distinct *Hosta* plant named 'Secret Ambition' as illustrated and described.

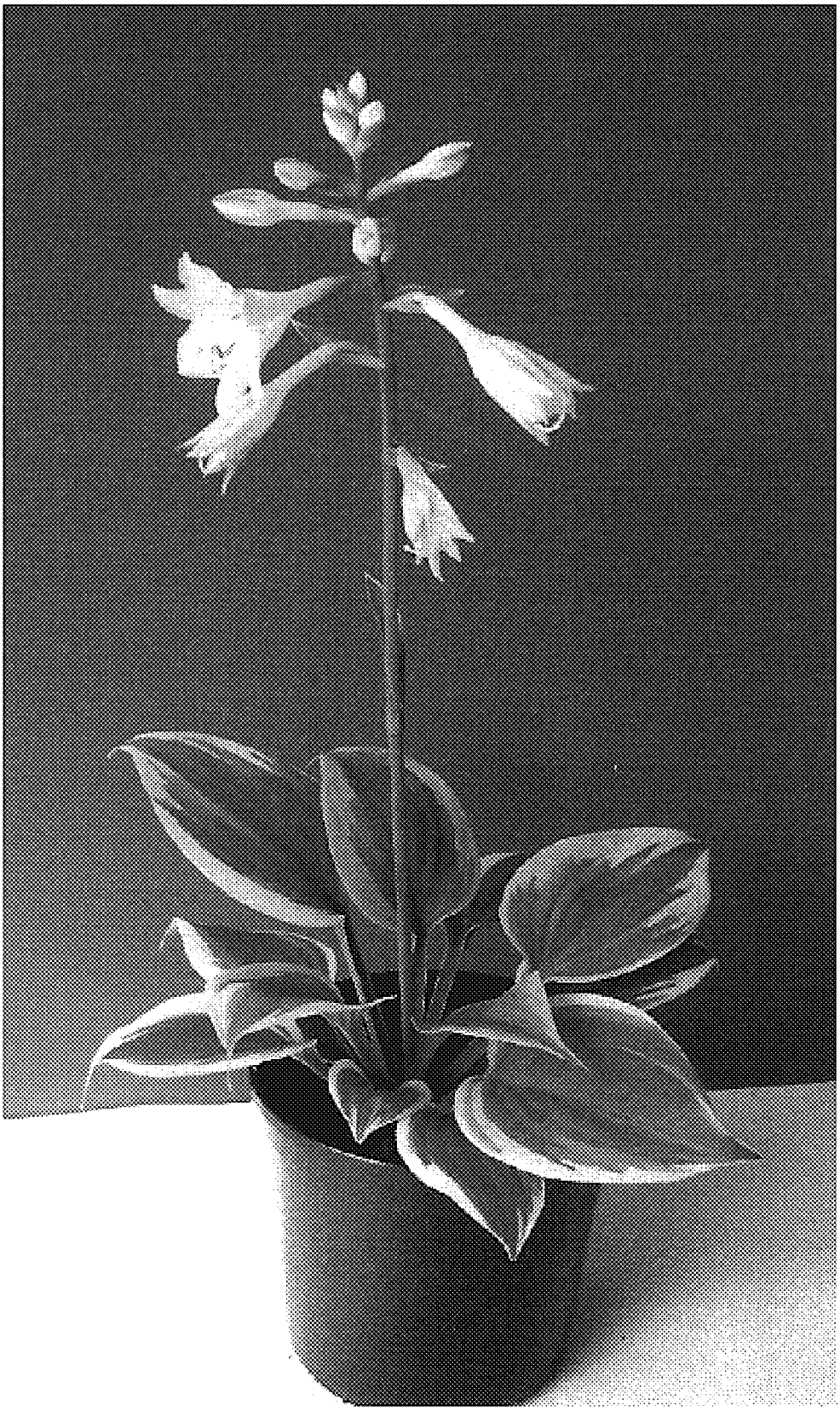

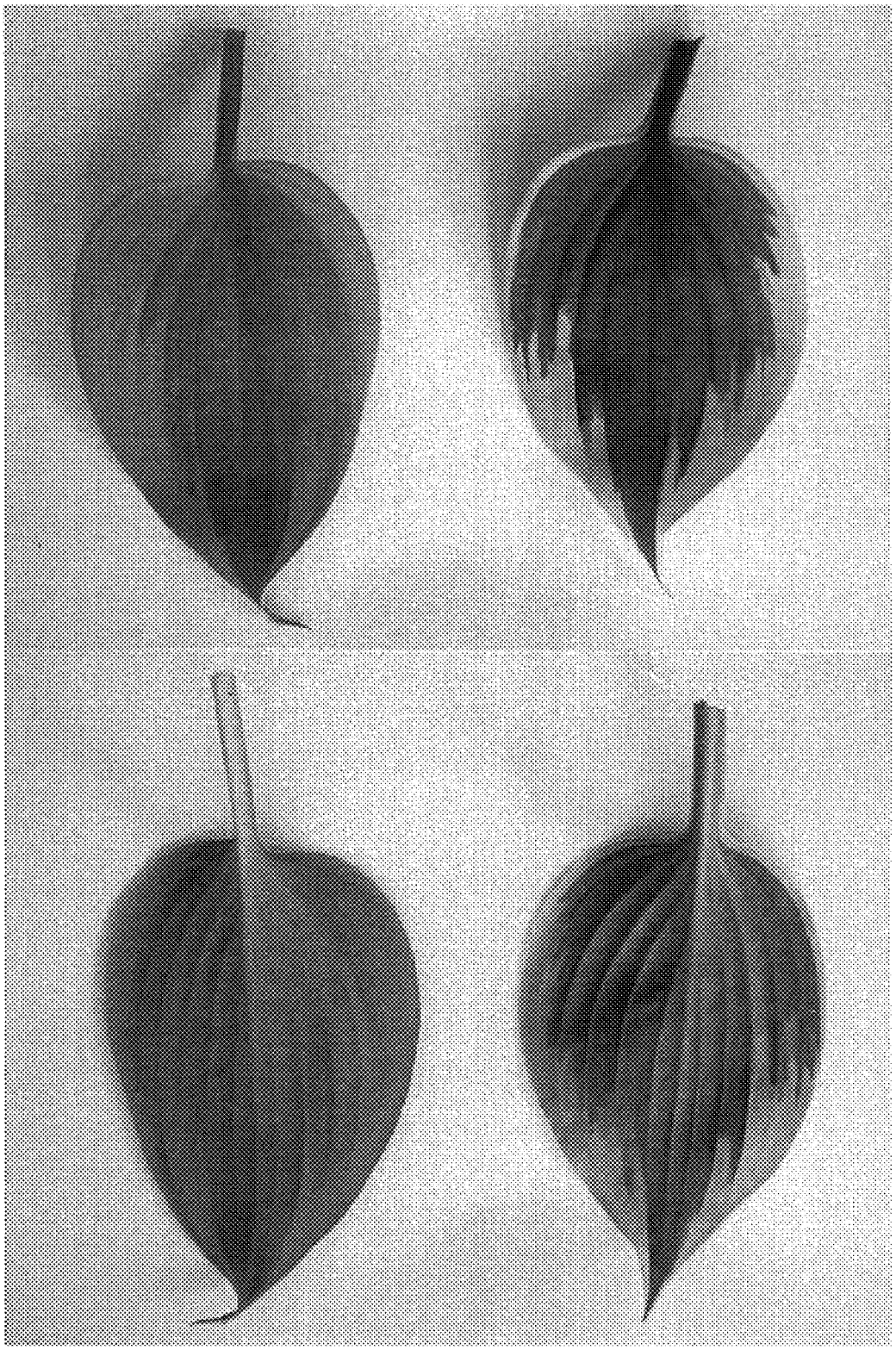

* * * * *